US008568429B2

(12) United States Patent
Kraemer et al.

(10) Patent No.: US 8,568,429 B2
(45) Date of Patent: *Oct. 29, 2013

(54) TRANSORAL ENDOSCOPIC GASTROESOPHAGEAL FLAP VALVE RESTORATION DEVICE, ASSEMBLY, SYSTEM AND METHOD

(75) Inventors: Stefan J. M. Kraemer, Seattle, WA (US); John M. Adams, Sammamish, WA (US); Stephen T. Vincent, Kirkland, WA (US)

(73) Assignee: EndoGastric Solutions, Inc., Redmond, WA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/547,026

(22) Filed: Jul. 11, 2012

(65) Prior Publication Data

US 2012/0277776 A1 Nov. 1, 2012

Related U.S. Application Data

(63) Continuation of application No. 13/103,933, filed on May 9, 2011, which is a continuation of application No. 10/864,946, filed on Jun. 10, 2004, now Pat. No. 7,942,887, which is a continuation of application No. 10/150,740, filed on May 17, 2002, now Pat. No. 6,790,214.

(51) Int. Cl.
*A61B 19/00* (2006.01)

(52) U.S. Cl.
USPC .......................................... 606/151; 606/153

(58) Field of Classification Search
USPC .......... 606/139–151, 153, 205–209, 219–220
See application file for complete search history.

(56) References Cited

U.S. PATENT DOCUMENTS

| 6,592,596 B1 * | 7/2003 | Geitz ............................. 606/139 |
| 6,773,441 B1 * | 8/2004 | Laufer et al. .................. 606/153 |
| 2002/0040226 A1 * | 4/2002 | Laufer et al. .................. 606/153 |
| 2002/0082621 A1 * | 6/2002 | Schurr et al. .................. 606/151 |
| 2011/0213390 A1 * | 9/2011 | Kraemer et al. ............... 606/153 |

* cited by examiner

*Primary Examiner* — Darwin Erezo
(74) *Attorney, Agent, or Firm* — Fulwider Patton LLP

(57) ABSTRACT

The invention provides a device, assembly, and method for transoral endoscopic restoration of a gastroesophageal flap valve. The invention also provides a self-steering and self-closing tissue fixation device for tissue fixation, and an invaginator device for gripping and maneuvering tissue. The restoration device includes a longitudinal member arranged for transoral placement into a stomach, a tissue shaper carried on the longitudinal member that causes stomach tissue to assume a shape related to a gastroesophageal flap, and a tissue fixation device that maintains the shaped stomach tissue in a shape approximating a gastroesophageal flap. The tissue shaper may include a mold. The device may include the invaginator device for gripping and maneuvering esophageal tissue to aid restoration of the gastroesophageal flap, and may include the tissue fixation device.

11 Claims, 9 Drawing Sheets

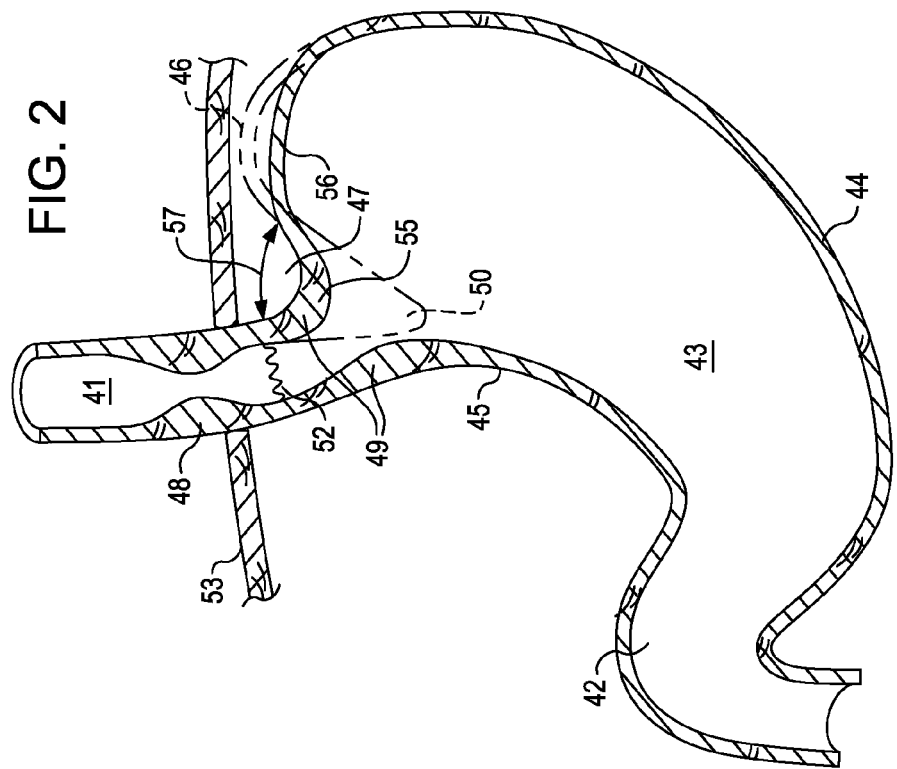
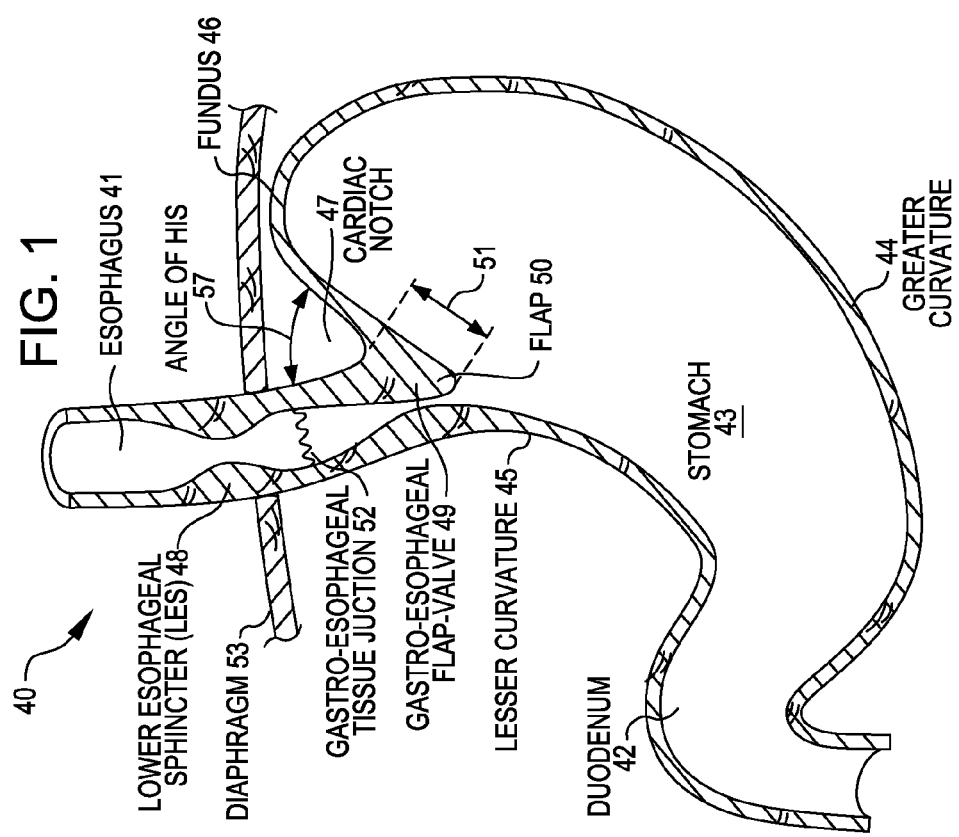

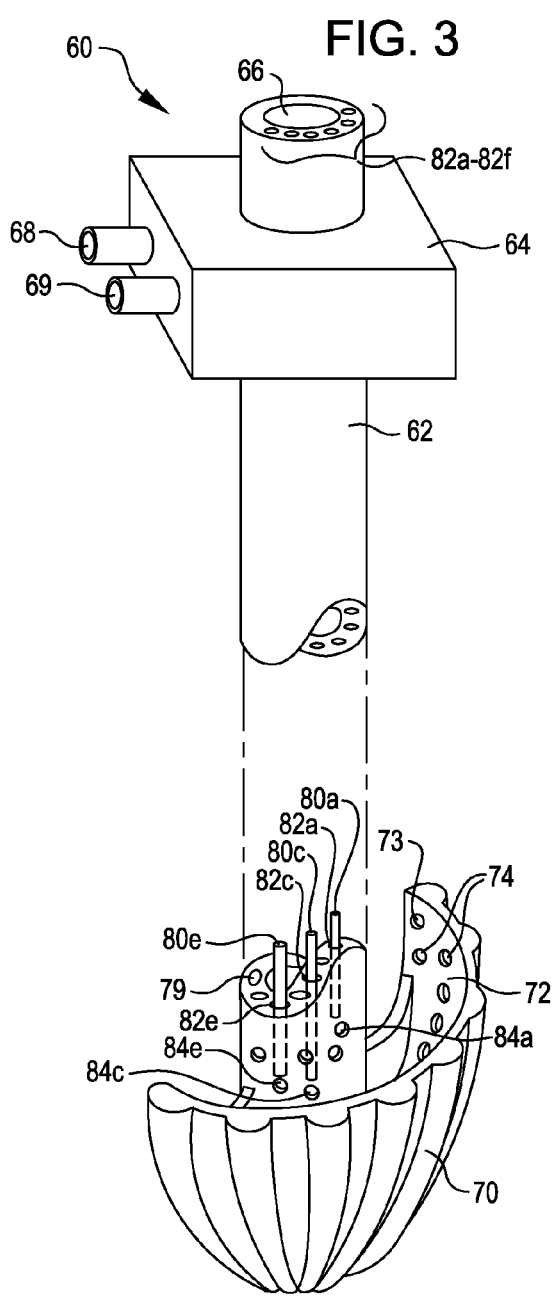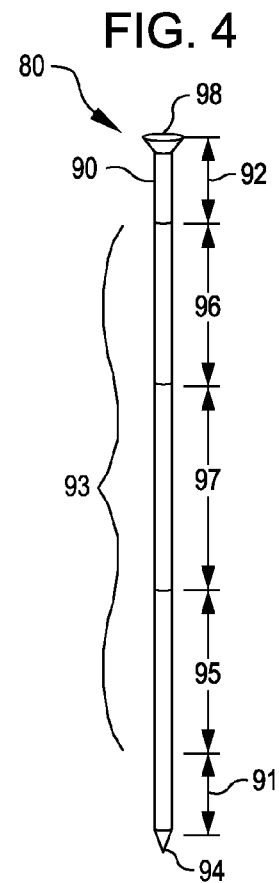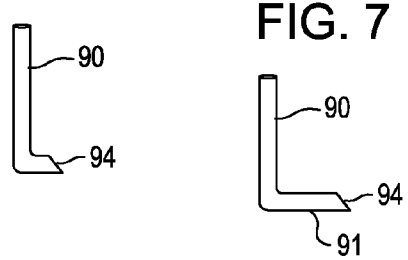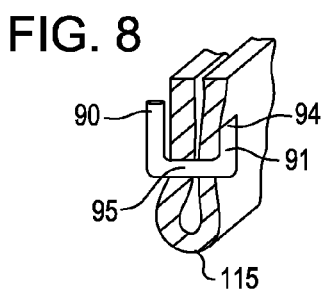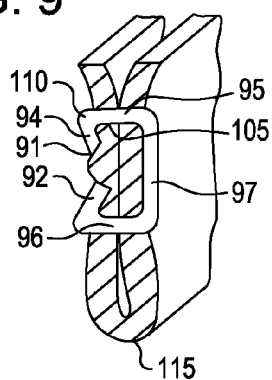

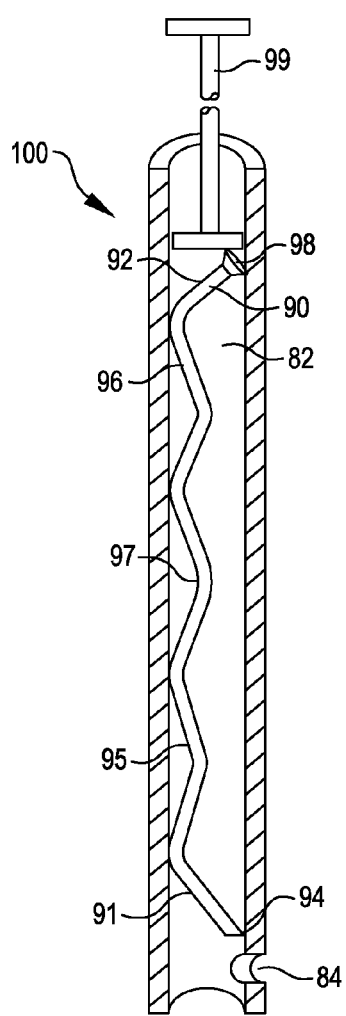
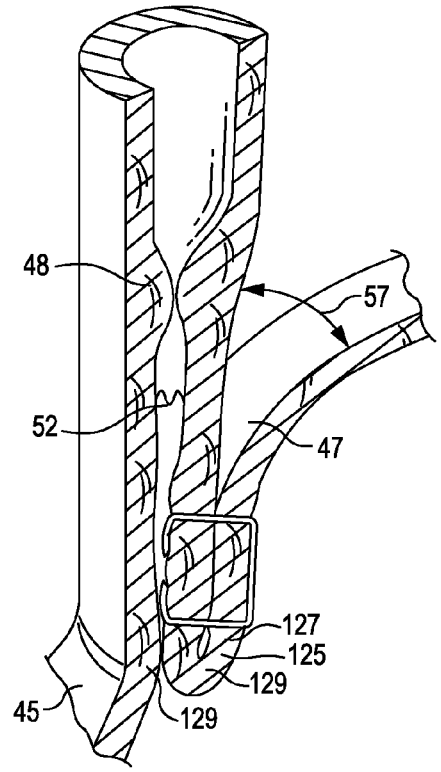
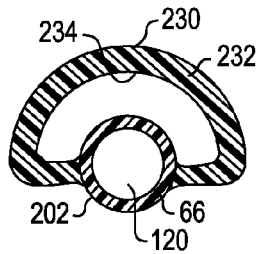
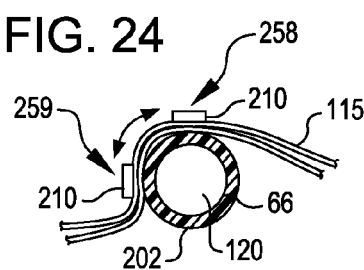
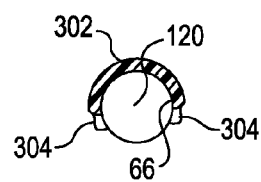

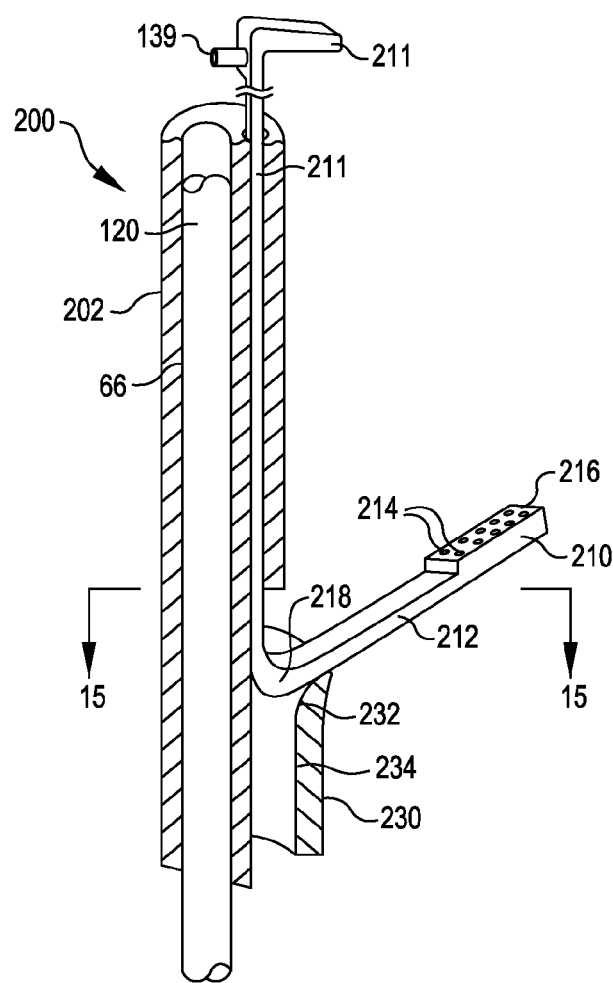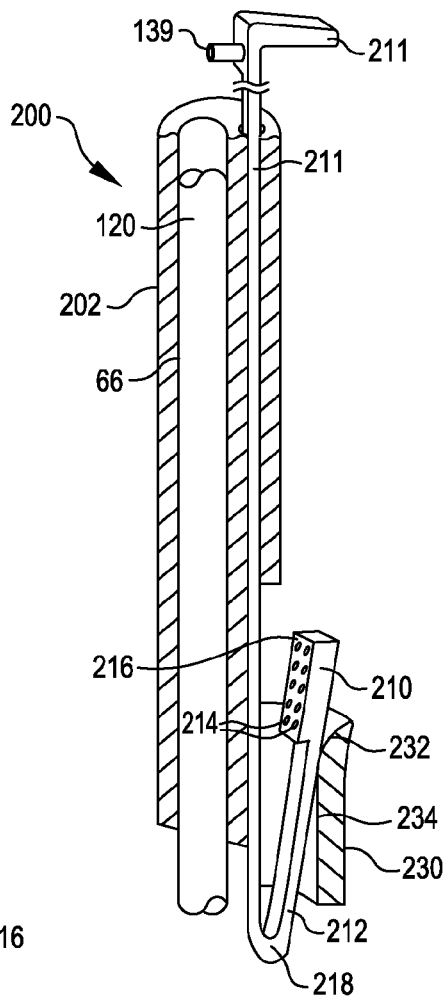

TRANSORAL ENDOSCOPIC GASTROESOPHAGEAL FLAP VALVE RESTORATION DEVICE, ASSEMBLY, SYSTEM AND METHOD

This application is a continuation of U.S. application Ser. No. 13/103,933, filed May 9, 2011, which is a continuation of U.S. application Ser. No. 10/864,946, filed Jun. 10, 2004, now U.S. Pat. No. 7,942,887, which is a continuation of U.S. application Ser. No. 10/150,740, filed May 17, 2002, now U.S. Pat. No. 6,790,214. The complete disclosures of which are hereby incorporated for all intents and purposes.

FIELD OF THE INVENTION

The present invention generally relates to a device, assembly, system, and method for treating gastroesophageal reflux disease by restoring the gastroesophageal flap valve. The present invention more particularly relates to restoring the gastroesophageal flap valve by drawing gastric tissue into a shape approximating a normal gastroesophageal flap and fixing the tissue into that shape.

BACKGROUND

Gastroesophageal reflux disease (GERD) is a chronic condition caused by the failure of the anti-reflux barrier located at the gastroesophageal junction to keep the contents of the stomach from splashing into the esophagus. The splashing is known as gastroesophageal reflux. The stomach acid is designed to digest meat, and will digest esophageal tissue when persistently splashed into the esophagus.

FIG. 1 is a front cross-sectional view of the esophageal-gastro-intestinal tract 40 from a lower portion of the esophagus 41 to the duodenum 42. The stomach 43 is characterized by the greater curvature 44 on the anatomical left side and the lesser curvature 45 on the anatomical right side. The fundus 46 of the greater curvature 44 forms the superior portion of the stomach 43, and traps gas and air bubbles for burping. The esophageal tract 41 enters the stomach 43 at a point below the superior portion of the fundus 46, forming a cardiac notch 47 and an acute angle with respect to the fundus 46 known as the Angle of His 57. The lower esophageal sphincter (LES) 48 is a discriminating sphincter able to distinguish between burping gas, liquids, and solids, and works in conjunction with the fundus 46 to burp. The gastroesophageal flap valve (GEFV) 49 includes a moveable portion and an opposing more stationary portion. The moveable portion of the GEFV 49 is an approximately 180 degree, semicircular, gastroesophageal flap 50 (alternatively referred to as a "normal moveable flap" or "moveable flap") formed of tissue at the intersection between the esophagus 41 and the stomach 43. The opposing more stationary portion of the GEFV 49 comprises a portion of the lesser curvature 45 of the stomach 43 adjacent to its junction with the esophagus 41. The gastroesophageal flap 50 of the GEFV 49 principally comprises tissue adjacent to the fundus 46 portion of the stomach 43, is about 4 to 5 cm long (51) at it longest portion, and the length may taper at its anterior and posterior ends. The gastroesophageal flap 50 is partially held against the lesser curvature 45 portion of the stomach 43 by the pressure differential between the stomach 43 and the thorax, and partially by the resiliency and the anatomical structure of the GEFV 49, thus providing the valving function. The GEFV 49 is similar to a flutter valve, with the gastroesophageal flap 50 being flexible and closeable against the other more stationary side.

The esophageal tract is controlled by an upper esophageal sphincter (UES) near the mouth for swallowing, and by the LES 48 and the GEFV 49 at the stomach. The normal antireflux barrier is primarily formed by the LES 48 and the GEFV 49 acting in concert to allow food and liquid to enter the stomach, and to considerably resist reflux of stomach contents into the esophagus 48 past the gastroesophageal tissue junction 52. Tissue aboral of the gastroesophageal tissue junction 52 is generally considered part of the stomach because the tissue protected from stomach acid by its own protective mechanisms. Tissue oral of the gastroesophageal junction 52 is generally considered part of the esophagus and it is not protected from injury by prolonged exposure to stomach acid. At the gastroesophageal junction 52, the juncture of the stomach and esophageal tissues form a zigzag line, which is sometimes referred to as the "Z-line." For the purposes of these specifications, including the claims, "stomach" means the tissue aboral of the gastroesophageal junction 52. As pressure in the stomach 43 increases, the pressure tightly closes the normal gastroesophageal flap 50 of the GEFV 49 against the lesser curve portion 45 of the stomach. The tissues are tightly opposed preventing reflux. The stomach 43 provides for burping by the diaphragm 53 pushing down on and flattening the fundus 46, temporarily resulting in the cardiac notch 47 being straightened and the Angle of His 57 becoming less acute. The normal gastroesophageal flap 50 of the GEFV 49 opens to allow the burp to pass into the esophagus 41.

FIG. 2 is a front cross-sectional view of the esophageal-gastro-intestinal tract 40 illustrating a Grade I normal appearance movable flap 50 of the GEFV 49 and a Grade IV reflux appearance gastroesophageal flap 55 of the GEFV 49. A principal reason for regurgitation associated with GERD is the mechanical failure of the deteriorated (or reflux appearance) gastroesophageal flap 55 of the GEFV 49 to close and seal against the high pressure in the stomach. Due to reasons including lifestyle, a Grade I normal gastroesophageal flap 50 of the GEFV 49 may deteriorate into a Grade IV deteriorated (or reflux appearance) gastroesophageal flap 55. The anatomical results of the deterioration include moving a portion of the esophagus 41 that includes the gastroesophageal junction 52 and LES 48 toward the mouth, straightening of the cardiac notch 47, and increasing the Angle of His 57. This effectively reshapes the anatomy aboral of the gastroesophageal junction 52 and forms a flattened fundus 56. The deteriorated gastroesophageal flap 55 illustrates a gastroesophageal flap valve 49 and cardiac notch 47 that have both significantly degraded. Dr. Hill and colleagues developed a grading system to describe the appearance of the GEFV and the likelihood that a patient will experience chronic acid reflux. L. D. Hill, et al., *The gastroesophageal flap valve: in vitro and in vivo observations*, Gastrointestinal Endoscopy 1996:44:541-547. Under Dr. Hill's grading system, the normal movable flap 50 of the GEFV 49 illustrates a Grade I flap valve that is the least likely to experience reflux. The deteriorated gastroesophageal flap 55 of the GEFV 49 illustrates a Grade IV flap valve that is the most likely to experience reflux. Grades II and III reflect intermediate grades of the likelihood of experiencing reflux. In the Grade IV condition with the deteriorated GEFV represented by deteriorated gastroesophageal flap 55 and the fundus 46 moved inferior, the stomach contents are presented a funnel-like opening directing the contents into the esophagus 41.

With the deteriorated gastroesophageal flap 55, the stomach contents are more likely to be regurgitated into the esophagus 41, the mouth, and even the lungs. The LES 48 by itself is relatively weak and does not provide sufficient resistance to prevent reflux or regurgitation by itself. The regurgitation is referred to as "heartburn" because the most common symptom is a burning discomfort in the chest under the breastbone. Burning discomfort in the chest and regurgitation (burping up) of sour-tasting gastric juice into the mouth are classic symptoms of gastroesophageal reflux disease (GERD). When stomach acid is regurgitated into the esophagus, it is usually cleared quickly by esophageal contractions. Heartburn (backwashing of stomach acid and bile onto the esophagus 41) results when stomach acid is frequently regurgitated into the esophagus 41, or if it is not promptly cleared. Chronic heartburn or GERD occurs because of a mechanical failure by the deteriorated gastroesophageal flap 55 of the GEFV 49 and the LES 48 to keep stomach acid and digestive juices out of the esophagus 41. The GEFV 49 and LES 48 fail to maintain the normally higher pressure in the stomach 43 and keep stomach contents out of the esophagus 41. People with a normal movable flap 50 may experience occasional transient GEFV 49 and LES 48 relaxations that lead to backwashing of stomach contents onto the esophagus 41. These transient relaxations account for most of the gastroesophageal reflux episodes and occasional symptoms in people with a normal gastroesophageal flap 50. However, because the deteriorated gastroesophageal flap 55 of GEFV 49 and the LES 48 are not mechanically able to maintain the normal pressure in the stomach 43, the stomach contents more readily and regularly bathe the esophagus 41. The esophageal contractions alone are not strong enough to adequately "strip" the stomach contents out of the esophagus 41, leading to prolonged acid and bile exposure in the esophagus. This prolonged exposure allows injury to the normal squamous lining of the esophagus to occur, resulting in esophagitis and in some people, healing of the esophagus with the development of a new lining, called Barrett's esophagus.

Complications develop for some people who have GERD. Esophagitis (inflammation of the esophagus) with erosions and ulcerations (breaks in the lining of the esophagus) can occur from repeated and prolonged acid exposure. If these breaks are deep, bleeding or scarring of the esophagus with formation of a stricture (narrowing of the esophagus) can occur. If the esophagus narrows significantly, then food sticks in the esophagus and the symptom is known as dysphagia. GERD has been shown to be one of the most important risk factors for the development of esophageal adenocarcinoma. In a subset of people who have severe GERD, if acid exposure continues, the injured squamous lining is replaced by Barrett's metaplasia (Barrett's esophagus), a precancerous lining in which esophageal adenocarcinoma can develop. To date, no one knows what causes Barrett's esophagus.

Other complications of GERD may not appear to be related to esophageal disease at all. Some people with GERD may develop recurrent pneumonia (lung infection), asthma (wheezing), or a chronic cough from acid backing up into the esophagus and all the way up through the upper esophageal sphincter into the lungs. In many instances, this occurs at night, while the person is sleeping. Occasionally, a person with severe GERD will be awakened from sleep with a choking sensation. Hoarseness can also occur due to acid reaching the vocal cords, causing a chronic inflammation or injury.

Deteriorated gastroesophageal flap 55 and GERD never improve without intervention. Both medical and surgical treatments exist for GERD. Medical therapies include antacids and proton pump inhibitors. However, the medical therapies only mask the reflux. Patients still get reflux and perhaps emphysema because of particles refluxed into the lungs. Barrett's esophagus results in about 10-15% of the GERD cases. The esophageal epithelium changes into tissue that tends to become cancerous from repeated acid washing despite the medication.

Several open laparotomy and laproscopic surgical procedures are available for treating GERD. One surgical approach is the Nissen fundoplication. The Nissen approach typically involves a 360-degree wrap of the fundus around the gastroesophageal junction 52. The procedure has a high incidence of postoperative complications. The Nissen approach creates a 360-degree moveable flap without a fixed portion. While Nissen reinforces the LES 48, it does not restore the normal movable flap 50 of GEFV 49. The patient cannot burp because the fundus 46 was used to make the repair, and may frequently experience dysphagia. Another surgical approach to treating GERD is the Belsey Mark IV (Belsey) fundoplication. The Belsey procedure involves creating a valve by suturing a portion of the stomach 43 to an anterior surface of the esophagus 41. It reduces some of the postoperative complications encountered with the Nissen fundoplication, but still does not restore the normal movable flap 50 of GEFV 49. None of these procedures fully restores the normal anatomical anatomy or produces a normally functioning gastroesophageal junction. Another surgical approach is the Hill repair. In the Hill repair procedure, the gastroesophageal junction 52 is anchored to the posterior abdominal areas, and a 180-degree valve is created by a system of sutures. The Hill procedure restores the moveable flap 50, the cardiac notch 47 and the Angle of His 57. However, all of these surgical procedures are very invasive, regardless of whether done as a laproscopic or an open procedure.

New, less surgically invasive approaches to treating GERD involve transoral endoscopic procedures. One procedure contemplates a machine device with robotic arms that is inserted transorally into the stomach 43. While observing through an endoscope, a endoscopist guides the machine within the stomach 43 to engage a portion of the fundus 46 with a corkscrew-like device on one arm. The arm then pulls on the engaged portion to create a flap of tissue near the deteriorated gastroesophageal flap 55. Another arm of the machine pinches the base of the flap, and drives staples and/or sutures through it to secure the flap. The endoscopist engages additional portions of the fundus 46 and drives additional staples until the endoscopist is satisfied with the flap produced. While the pinch-and-staple procedure may provide a measure of treatment in appropriate hands, it neither fully restores the normal gastroesophageal flap valve anatomy nor produces a normally functioning gastroesophageal junction 52. Instead, the procedure only creates a tissue bulge that may assist in limiting reflux. Furthermore, this procedure is highly dependent on the skill, experience, aggressiveness, and courage of the endoscopist. A more timid endoscopist may take only small bites of tissue, and as a result may not successfully create a flap that functions as a normal movable flap 50. Every flap built with this procedure will be different because it depends so much on the skill and courage of the physician. Another transoral procedure contemplates making a fold of fundus tissue near the deteriorated gastroesophageal flap 55 to recreate the LES. The procedure requires placing multiple U-shaped tissue clips around the folded fundus to hold it in shape and in place. Like the previously discussed procedure, this procedure is also highly dependent on the skill, experience, aggressiveness, and courage of the endoscopist. In addition, these and other procedures may involve esophageal tissue in the repair. Esophageal tissue is fragile and weak, and involvement of esophageal tissue in the repair of a gastroesophageal flap valve poses unnecessary risks to the patient.

Present and emerging methods all depend on the skill, experience, and aggressiveness of the endoscopist to grasp the appropriate amount of stomach or esophagus tissue to build the depth and width of the structure contemplated. This results in non-uniformity from patient to patient and non-uniformity from endoscopist to endoscopist. There is a need for a highly standardized and uniform device and procedure for restoring the natural gastroesophageal flap valve and a normally functioning gastroesophageal junction.

In view of the foregoing, there is a need in the art for a new and improved apparatus and method for restoration of a gastroesophageal flap valve. The present invention is directed to a device, system, and method that provide such an improved apparatus and method for restoration of a gastroesophageal flap valve.

SUMMARY

The invention provides a transoral endoscopic gastroesophageal flap valve restoration device. The device includes a longitudinal member arranged for transoral placement into a stomach, a tissue shaper carried on the longitudinal member that causes stomach tissue to assume a shape related to a gastroesophageal flap, and a tissue fixation device that maintains the shaped stomach tissue in a shape approximating a gastroesophageal flap. The tissue shaper may include a tissue gripper. The tissue fixation device may include a self-steering and self-closing device having an elongated member having a first end portion and a second end portion, the first end portion terminating in a tissue-piercing end, and a connecting portion extending between the first and second end portions, the connecting portion having a first and second joining portions separated by a pressure portion. The elongated member has an initial stressed and distorted configuration that, as the portions beginning with the first end portion are deployed from a lumen by a force pushing on the second end portion, steers the elongated member into and through tissue proximate to the lumen and assumes a final configuration, wherein the elongated member forms an interior perimeter holding together tissue enclosed within the perimeter.

The invention further provides a transoral endoscopic gastroesophageal flap valve restoration assembly. The assembly includes a longitudinal member arranged for transoral placement into a stomach and that carries a mold having a shape related to a gastroesophageal flap, a tissue shaper that non-invasively grips and urges tissue into the mold, and a tissue fixation device that maintains the molded stomach tissue in a shape approximating a gastroesophageal flap. The mold may have a first configuration for transoral placement in proximity to the gastroesophageal junction, and a second configuration having the shape related to the gastroesophageal flap valve. The mold may be further arranged to move from the first configuration to the second configuration in vivo. The mold may also be further arranged to move from the first configuration to the second configuration in response to a change in pressure in a portion of the mold. The mold may have a first configuration for transoral placement in proximity to the esophageal-gastric junction, a second configuration having the shape related to the gastroesophageal flap valve, and a third configuration for transoral removal. The first configuration and third configuration may be similar. The mold may be made from any biocompatible material known in the art, may have a shape related to a gastroesophageal flap that is transparent. The mold may include a material that is passed "per vias naturales," including a material that is degradable or digestible within the digestive system and passed out of the body, or simply passed out of the body. The molded stomach tissue may form an approximately 180 degree, semicircular structure. In alternative embodiments, the mold may be configured to form a semicircular structure having with a semicircular arc varying between approximately 90 degrees and 360 degrees.

In accordance with a further embodiment of the present invention, the longitudinal member may include a channel arranged to maintain an orientation with the endoscope. The longitudinal member may be arranged to at least partially surround a length of an endoscopic device, and be moveable relative to the length of the endoscopic device. Further, the longitudinal member may be arranged to engage an extracorporeal portion of a shaft of an endoscopic device when a distal portion of the endoscopic device is in vivo, and be moveable relative to the shaft of the endoscopic device. The longitudinal member may include at least one lumen arranged to carry at least one tissue fixation device. The longitudinal member may further comprise an extracorporeal member providing movement control. The longitudinal member may carry the tissue shaper. The tissue shaper may grip tissue with a vacuum, and may further include a plurality of vacuum orifices on at least a portion of a molding surface of the mold arranged to draw tissue into the mold and hold the tissue proximate to the molding surface. The tissue shaper may include a structure that moves from a first position arranged to grip tissue to a second position arranged to urge tissue into the mold, and a member carried on the structure and having a plurality of vacuum orifices on a surface arranged to grip tissue. The tissue shaper may be movable with respect to the mold. The fixation device may include a self-steering and self-closing tissue fixation device that includes an elongated member having a first end portion and a second end portion, the first end portion terminating in a tissue-piercing end, and a connecting portion extending between the first and second end portions, the connecting portion having first and second joining portions separated by a pressure portion. The elongated member has an initial stressed and distorted configuration that, as the portions beginning with the first end portion are deployed from a lumen by a force pushing on the second end portion, steers the elongated member into and through tissue proximate to the lumen and assumes a final configuration, wherein the elongated member forms an interior perimeter holding together tissue enclosed within the perimeter. The elongated member of the tissue fixation device may form a substantially enclosed interior perimeter when the elongated member is in the final configuration.

The present invention further provides a transoral endoscopic gastroesophageal flap valve restoration assembly. The assembly includes a longitudinal member arranged for transoral placement into a stomach that carries a mold having a shape related to a gastroesophageal flap, a tissue griper that non-invasively grips with a vacuum and urges tissue to take a shape related to the mold, an invaginator having a tissue gripper to vacuum grip esophageal tissue and allow a force to be imparted to the vacuum gripped esophageal tissue, and a tissue fixation device that maintains the molded stomach tissue in a shape approximating a gastroesophageal flap. The invaginator may have a first configuration for transoral placement in the esophagus, and a second configuration for vacuum engagement with the esophageal tissue, which may be in response to a change in pressure in a portion of the invaginator. The invaginator may be further arranged to move from the first configuration to the second configuration in vivo. The invaginator may include an extracorporeal member providing movement control, may be arranged to be carried on an endoscopic device, and may have a channel arranged to maintain an orientation with an endoscopic device. The invaginator may also have a channel arranged to maintain an orientation with the mold. The invaginator may further include a plurality of vacuum orifices opening on at least a portion of the peripheral surface of the invaginator and arranged to hold tissue proximate to at least a portion of the peripheral surface. The invaginator may allow a force to be imparted to the vacuum gripped esophageal tissue sufficient to move stomach tissue into an improved position for restoration of a gastroesophageal flap. The invaginator may be made from any biocompatible material known in the art.

The invention provides for yet another embodiment providing a transoral endoscopic gastroesophageal flap valve restoration assembly. The assembly includes a longitudinal member arranged for transoral placement into a stomach, and that carries a mold having a shape related to a gastroesophageal flap. The longitudinal member further has a channel arranged to maintain an orientation with an endoscopic device, and a lumen or other type of chamber arranged to carry a tissue fixation device. The assembly also includes a tissue gripper that non-invasively grips with a vacuum and urges tissue to take a shape related to the mold, the tissue gripper including a member carried on the longitudinal member that has a plurality of vacuum orifices on a surface arranged to grip tissue and hold the tissue proximate to a molding surface of the mold. The assembly further includes a self-steering and self-closing tissue fixation device that maintains the molded stomach tissue in a shape approximating a gastroesophageal flap, the tissue fixation device having an elongated member having a first end portion and a second end portion, the first end portion terminating in a tissue-piercing end, and a connecting portion extending between the first and second end portions, the connecting portion having a first and second joining portions separated by a pressure portion. The elongated member has an initial stressed and distorted configuration that, as portions beginning with the first end portion are deployed from a lumen by a force pushing on the second end portion, steers the elongated member into and through tissue proximate to the lumen and assumes a final configuration, wherein the elongated member forms an interior perimeter holding together tissue enclosed within the perimeter.

The invention provides for a self-steering and self-closing tissue fixation device for effecting tissue geometry. The tissue fixation device includes an elongated member having a first end portion and a second end portion, the first end portion terminating in a tissue-piercing end, and a connecting portion extending between the first and second end portions, the connecting portion having a first and second joining portions separated by a pressure portion. The elongated member has an initial stressed and distorted configuration that, as portions beginning with the first end portion are deployed from a lumen by a force pushing on the second end portion, steers the elongated member into and through a fold of tissue proximate to the lumen and assumes a final configuration, wherein the elongated member forms an interior perimeter holding together the fold of tissue enclosed within the perimeter. The elongated member may form a substantially enclosed interior perimeter when the elongated member is in the final configuration. The first end portion may be proximate to the second end portion when the elongated member is in the final configuration. The elongated member may form an approximately rectangular interior perimeter in the final configuration. The elongated member may form an approximately round interior perimeter in the final configuration. The elongated member may be formed from material having superelastic and shape memory properties, including Nitinol, or from a plastic material having shape memory.

Still another embodiment of the invention provides an invaginator device comprising a member arranged to vacuum grip interior tissue of a hollow body structure and allow a force to be imparted on the hollow body structure. The member may have a first configuration for placement in the hollow body structure, and a second configuration for vacuum gripping of the hollow body structure. The member may be further arranged to move from the first configuration to the second configuration in vivo, which may be in response to a change in pressure in an expandable portion of the device. The invaginator may further comprise a plurality of vacuum orifices opening on at least a portion of the peripheral surface of the invaginator and arranged to hold tissue proximate to at least a portion of the peripheral surface. The invaginator may allow a force to be imparted to the vacuum gripped esophageal tissue sufficient to move stomach tissue into an improved position for restoration of a gastroesophageal flap. The invaginator may include an extracorporeal portion providing movement control, may be arranged to be carried on an endoscopic device, and may include a channel arranged to maintain an orientation with an endoscopic device.

In accordance with still yet another embodiment, the present invention provides a method of transoral restoration of a gastroesophageal flap valve. The method includes the steps of selecting a portion of intraluminal fundus tissue that is proximate to the cardiac notch or another portion of the gastric wall, shaping the tissue into a shape resembling a gastroesophageal flap, and fixating the shaped tissue into a shape approximating a gastroesophageal flap. The fixating step may include deploying a self-steering and self-closing device. The shaping step may include molding the tissue into a shape resembling a gastroesophageal flap.

In another embodiment, the present invention provides a method of transoral restoration of a gastroesophageal flap valve. The method includes the steps of providing at least one self-steering and self-closing tissue fixation device for effecting gastroesophageal geometry, and providing a longitudinal member carrying a mold having a shape related to a gastroesophageal flap valve, and a tissue shaper that urges gastric tissue to take a shape related to the mold, the tissue gripper including a member having a plurality of vacuum orifices on a surface arranged to grip tissue and to hold the tissue proximate to a molding surface of the mold. The method further includes the steps of placing at least one tissue fixation device into a lumen in the longitudinal member arranged to carry a tissue fixation device, locating the mold proximate to the gastroesophageal junction, gripping gastric tissue from the fundus region of the stomach proximate to the cardiac notch with the tissue shaper and urging the gastric tissue into a shape related to a gastroesophageal flap, and pushing at least one tissue fixation device from the lumen and into the gastric tissue to maintain the gastric tissue in a shape approximating a gastroesophageal flap. The method may further include the step of applying a force with an invaginator to the vacuum gripped esophageal tissue sufficient to move stomach tissue into an improved position for restoration of a gastroesophageal flap.

These and various other features as well as advantages which characterize the present invention will be apparent from a reading of the following detailed description and a review of the associated drawings.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawings, in the several figures of which like referenced numerals identify like elements, and wherein:

FIG. 1 is a front cross-sectional view of the esophageal-gastro-intestinal tract from a lower portion of the esophagus to the duodenum;

FIG. 2 is a front cross-sectional view of the esophageal-gastro-intestinal tract illustrating a Grade I normal appearance movable flap of the gastroesophageal flap valve and a Grade IV reflux appearance gastroesophageal flap of the gastroesophageal flap valve;

FIG. 3 is a perspective partial-sectional view of a gastroesophageal flap valve restoration assembly including a mold of the normal movable flap according to an embodiment of the invention;

FIG. 4 is a plan view of a self-steering and self-closing tissue fixation device according to an embodiment of the invention;

FIG. 5 is a side view of the self-steering and self-closing tissue fixation device of FIG. 4 carried in a lumen, and in its initial stressed and distorted configuration;

FIGS. 6-9 illustrate sequential configurations of the self-steering and self-closing tissue fixation device as it is deployed and moves from an initial configuration to a final configuration;

FIG. 11 is a perspective cross-sectional view of a restored gastroesophageal flap and a restored gastroesophageal flap valve according to an embodiment of the invention;

FIG. 14 is a perspective partial-sectional view of a gastroesophageal flap valve restoration assembly with a moveable tissue gripper in an extended configuration, according to an embodiment of the invention;

FIG. 15 is a cross-sectional plan view of the mold of FIG. 14;

FIG. 16 is a perspective partial-sectional view of a gastroesophageal flap valve restoration assembly of FIG. 14 with the moveable tissue gripper in a retracted/molding configuration, according to an embodiment of the invention;

FIG. 24 is a cross-sectional view illustrating the gastroesophageal flap valve restoration assembly of FIG. 23 being used to transorally restore a gastroesophageal flap valve, according to an embodiment of the invention;

FIG. 26 is a perspective partial cross-sectional view of gastroesophageal flap valve restoration assembly of FIG. 25.

DETAILED DESCRIPTION

Figure 10:
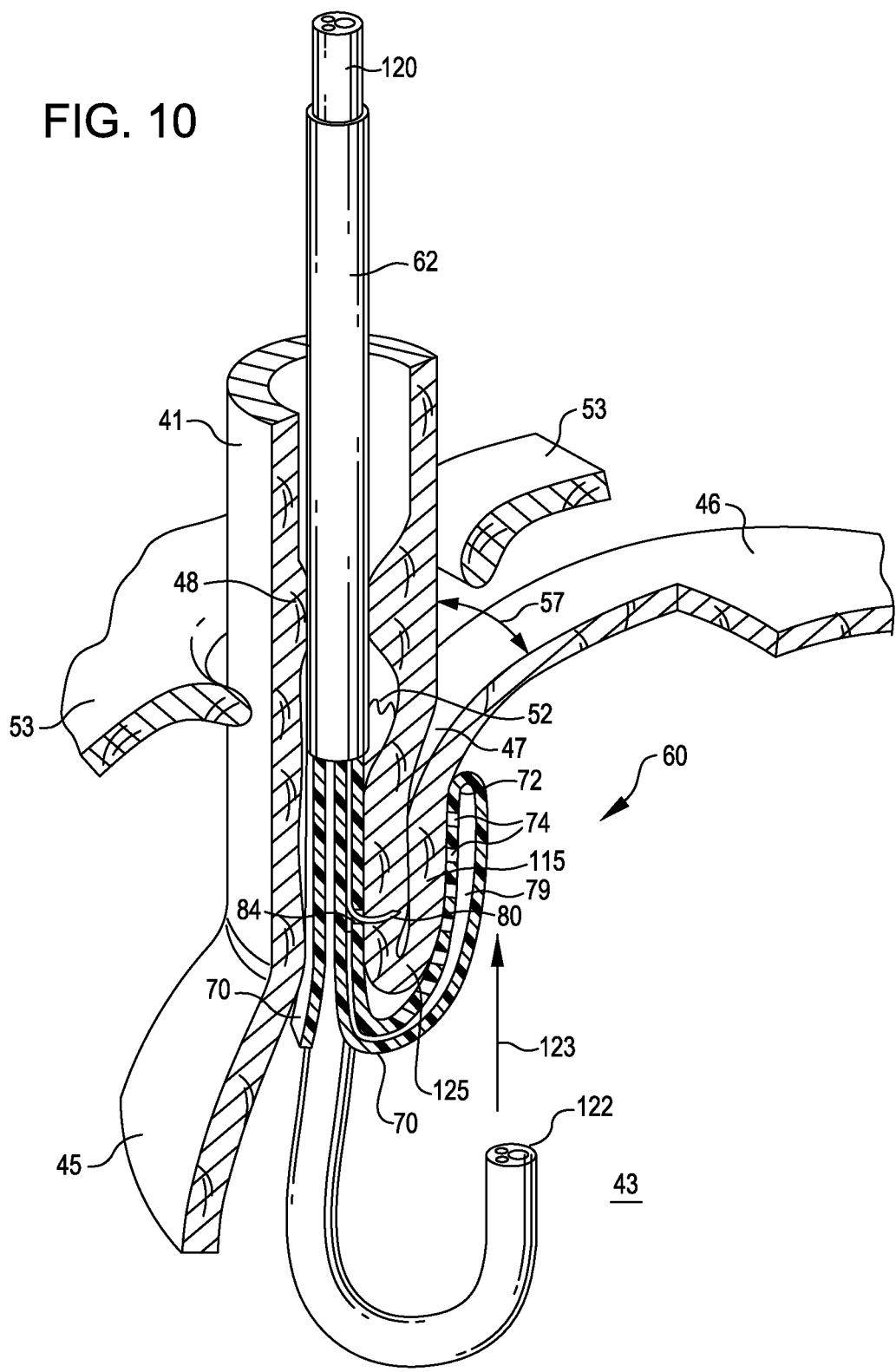
FIG. 10 is a perspective cross-sectional view of the gastroesophageal flap valve restoration assembly of FIG. 3 being used to transorally restore a gastroesophageal flap valve employing an endoscopic visualization device, according to an embodiment of the invention.

In the following detailed description of exemplary embodiments of the invention, reference is made to the accompanying drawings, which form a part hereof. The detailed description and the drawings illustrate specific exemplary embodiments by which the invention may be practiced. These embodiments are described in sufficient detail to enable those skilled in the art to practice the invention. It is understood that other embodiments may be utilized, and other changes may be made, without departing from the spirit or scope of the present invention. The following detailed description is therefore not to be taken in a limiting sense, and the scope of the present invention is defined only by the appended claims.

The meaning of "a", "an", and "the" include plural references. The meaning of "in" includes "in" and "on." Additionally, a reference to the singular includes a reference to the plural unless otherwise stated or inconsistent with the disclosure herein.

FIG. 3 is a perspective partial-sectional view of a gastroesophageal flap valve restoration assembly 60 including a mold of the normal movable flap 70 (hereafter "mold") 70 according to an embodiment of the invention. The GEFV restoration assembly 60 includes a longitudinal member 62, an extracorporeal movement control member 64, an endoscopic channel 66, a pressurized air port 68, a vacuum port 69, a mold 70 having a molding surface 72, a tissue shaper 73, a plurality of tissue fixation devices 80a, 80c, and 80e, a plurality of lumens 82a-e, and a plurality of lumen orifices 84a-e.

Longitudinal member 62 is a flexible structure dimensioned and structured for transoral placement into the esophagus and stomach, and includes the endoscopic channel 66 and the extracorporeal movement control member 64. Endoscopic channel 66 is arranged to at least partially surround a length of the shaft of an endoscopic device, maintain an orientation to the shaft, and be movable along the shaft. Longitudinal member 62 also includes the plurality of lumens 82a-e, each arranged to carry at least one tissue fixation device for deployment from the orifice of the lumen. FIG. 3 illustrates longitudinal member 62 carrying tissue fixation devices 80a, 80c, and 80e for deployment from the lumen orifices 84a, 84c, and 84e. In alternative embodiments, greater or fewer lumens 82 may be employed, and one lumen 82 may be arranged to deploy a plurality of tissue fixation devices 80. In a further alternative embodiment, the tissue fixation devices 80 may be carried in a chamber or a plurality of chambers, and deployed from the chambers. Longitudinal member 62 has sufficient flexibility for transoral placement into the stomach, and sufficient rigidity to manipulate structures carried by it. Longitudinal member 62 may be made from any material suitable for gastroesophageal surgical use, and suitable materials include any biocompatible material known in the art.

Extracorporeal movement control member 64 is rigidly attached to longitudinal member 62 and arranged for control of longitudinal and rotational movements of the longitudinal member 62, and any structures carried by it. While control member 64 is illustrated as carrying pressurized air port 66 and vacuum port 69, these ports may be carried on longitudinal member 62 or any other portion of flap valve restoration assembly 60. Control member 64 may be made from any biocompatible material known in the art.

Mold 70 is carried on the longitudinal member 62, and includes the molding surface 72 and the tissue gripper in the form of the plurality of tissue gripping vacuum orifices 74. The molding surface 72 has an approximately 180 degree, semicircular shape related to the normal movable flap 50 of GEFV 49, and resembles a cupped hand. In an embodiment, the molding surface 72 is formed to replicate the normal gastroesophageal flap 50. Observations of the normal gastroesophageal flap 50 have shown that the appearance, dimensions, and configuration do not vary significantly between people. Molding surface 72 is arranged to mold stomach tissue for fixation, such that when the molded stomach tissue is fixated and released from the mold 70, the molded stomach tissue has a shape and functionality approximating the normal gastroesophageal flap 50 of GEFV 49. Mold 70 is removably carried on longitudinal member 62, allowing for substitution of another mold 70 if it is discovered that a different molding surface 72 will provide a molded stomach tissue better approximating a GEFV 49.

In the embodiment illustrated in FIG. 3, the tissue shaper 73 includes a plurality of tissue gripping vacuum orifices 74 that cause stomach tissue to assume a shape related to the normal gastroesophageal flap 50 of GEFV 49. The vacuum orifices 74 are disposed on at least a portion of the molding surface 72. The vacuum orifices 74 are arranged to draw and urge selected proximate stomach tissue into the mold 70 and to form a molded stomach tissue 125 in a shape related to the normal gastroesophageal flap 50 of GEFV 49 in response to the molding surface 72. Vacuum orifices 74 are coupled to a vacuum source by the vacuum port 69 and by a vacuum lumen 79. The vacuum level at the vacuum orifices 74 is controlled by a regulator (not shown).

Mold 70 has a first configuration for transoral placement into proximity to the gastroesophageal junction, the placement being most likely into the stomach 43. The first configuration is a collapsed shape sized for the transoral placement. In an preferred embodiment, the collapsed shape maintains the endoscopic channel 66 so that the collapsed flap valve restoration assembly 60 may be transorally guided by an endoscope with its distal end placed in the stomach 43. Mold 70 has a second configuration, which has a shape related to the normal gastroesophageal flap 50 of GEFV 49 as illustrated in FIG. 3. Mold 70 is moved from the first configuration to the second configuration in vivo. Methods for moving from the first configuration to the second configuration include applying pressurized air to inflate mold 70, and a mechanical means. If the mold 70 is moved from the first configuration to the second configuration by applying pressurized air, flap valve restoration assembly 60 includes a pressurized air port 68 and a regulator (not shown) to provide a controlled air pressure, and an inflatable member (not shown). The inflatable member is coupled to the controlled air pressure by an air pressure lumen (not shown), and application of air pressure causes the mold 70 to move from the first configuration to the second configuration. Mold 70 is arranged to move from the second configuration to a third configuration for removal from the patient. The third configuration may be similar to the first configuration, or may be dissimilar. For example, mold 70 could move from the first configuration to the second configuration like an umbrella being unfolded. For transoral removal, mold 70 could then move back to the first configuration, or move to new configuration like an umbrella folded back in the wind. In an alternative embodiment, mold 70 comprises a material that may be passed "per vias naturales," and the third configuration includes releasing the mold 70 from the longitudinal member 62 into the stomach for passage "per vias naturales." Mold 70 is made from any biocompatible material known in the art. When arranged for passage "per vias naturales," the mold 70 may include a material that is degradable or digestible within the digestive system and passed out of the body, or simply passed out of the body.

In a preferred embodiment, the portion of the mold having a shape related to the GEFV is transparent so the endoscopist may visually confirm the shape of the molded stomach tissue prior to deploying the tissue fixation devices 82. In another alternative embodiment, the plurality of lumens 82a-e and lumen orifices 84a-e may be included in the mold 70 instead of longitudinal member 62.

In an alternative embodiment, the mold 70 may be coupled to an endoscopic device, and the endoscopic device used to maneuver the mold 70.

The next series of figures relate to the tissue fixation device, which is a self-steering and self-closing tissue fixation device in a preferred embodiment. FIG. 4 is a plan view of a self-steering and self-closing tissue fixation device (hereafter "tissue fixation device 80") according to an embodiment of the invention. FIG. 5 is a side view of the tissue fixation device of FIG. 4 carried in a lumen 82 and in its initial stressed and distorted configuration 100, according to an embodiment of the invention. FIGS. 6-9 illustrate sequential configurations of the tissue fixation device 80 as it is deployed and moves from an initial configuration 100 to a final configuration 115, according to an embodiment of the invention. Tissue fixation device 80 includes an elongated member 90, a first end portion 91, a second end portion 92, a connecting portion 93, a tissue-piercing end 94, a first joining portion 95, a second joining portion 96, a pressure portion 97, and a push-receiving end 98.

The elongated member 90 includes a biocompatible material having properties that allow it to move from a first configuration to a second configuration, typically upon release of a stress or distortion, or upon a change in temperature. Suitable materials include materials having superelastic properties, shape memory properties, or both. These materials include Nitinol that has both a shape memory and superelastic properties, and plastics having shape memory properties. The elongated member 90 is formed such that it has an initial stressed and distorted configuration 100, and a final configuration 110 arranged to hold together tissue enclosed within an interior perimeter 105. The overall length and thickness of the elongated member 90 are selected to provide the desired fixation by the elongated member 90. For example, the length of the portions may be selected depending on the type and thickness of the tissue fold 115 to be fixated and the amount of fixation force to be provided. The thickness of the elongated member 90 may be selected based on the amount of fixation force to be provided. The thickness may be between approximately 0.010 and 0.050 of an inch. Furthermore, the desired shape of the final configuration 110 may also determine the length of the portions and the thickness of the material, as well as the amount of bend between the portions in the final configuration 110. In alternative embodiments, the shape of the final configuration 110 may be generally rectangular, round, oval or mound. In a further alternative embodiment, the shape of the final configuration may generally be a spiral.

The initial stressed and distorted configuration 100 is arranged such that, as the portions beginning with the first end portion 91 are deployed from the lumen orifice 84 by a force imparted by push rod 99 on the push receiving end 98 of the second end portion 92, the superelastic and/or shape memory properties of tissue fixation device 80 steer the elongated member 90 into and through a fold of tissue 115 proximate to the lumen 84. In an alternative embodiment, the structure from which the tissue fixation device 80 is deployed may be arranged to provide at least part of the steering of elongated member 80. The deployment of tissue fixation device 80 is illustrated in FIGS. 6-9. Upon being completely pushed from the lumen 82, elongated member 90 self-closes to assumes a final configuration 110 illustrated in FIG. 9. In the final configuration 110, the elongated member 90 forms an interior perimeter 105 holding together the fold of tissue 115 that is enclosed within the perimeter. In the final configuration 110, the pressure portion 97 opposes the first end portion 91 and the second end portion 92, fixating the tissue fold 115 between them. The interior perimeter 105 of the final configuration 110 may close only to the degree necessary to provide the desired fixation. In an alternate embodiment, the first end portion 91 is proximate to second end portion 92 in the final configuration 110 as illustrated in FIG. 9. In a further alternative embodiment, the elongated member 90 forms a substantially enclosed perimeter in the final configuration 110.

FIG. 10 is a perspective cross-sectional view of the GEFV restoration assembly 60 of FIG. 3 being used to transorally restore a gastroesophageal flap valve employing an endoscopic visualization device 120, according to an embodiment of the invention. Endoscopic visualization is used in a preferred embodiment of restoring a GEFV. In other preferred embodiments, other visualization techniques may be used such as a fluoroscope or a swallowable camera. As shown in FIG. 10, a first step in transorally restoring a GEFV includes advancing a flexible endoscope 120 into the stomach 43 by way of the esophagus 41. The endoscope 120 is retroflexed so that the viewing element in the distal end 122 shows the area where the esophagus 41 joins the stomach 43. Viewing endoscopes are well known in the art, and are typically equipped with a lighting element and a viewing element enabling the operator to view the interior of a body cavity, such as the stomach 43 in this case. For the purposes of the embodiment of the invention illustrated in FIG. 10, the endoscopic visualization device (hereafter "endoscope") 120 may be an instrument separate from the other devices used to transorally restore a gastroesophageal flap valve. The endoscope 120 may work cooperatively with the other devices used to transorally restore a gastroesophageal flap valve, for example guiding the longitudinal member 62.

In an initial step, the longitudinal member 62 carrying the mold 70 is slid over the shaft of the endoscope 120 and placed near the proximal end of the endoscope 120. In another step, the viewing element of distal end 122 of the endoscope 120 is placed into the stomach 43, and retroflexed to provide viewing of the area where the esophagus 41 joins the stomach 43. The GEFV mold 70, in its first configuration for transoral placement, is lowered into the stomach 43 by sliding the longitudinal member 62 along the shaft of the endoscope 120 as a guide. Once in the stomach 43, the GEFV 70 mold is moved from its first configuration to its second configuration having a shape related to the GEFV 49. Another step includes moving the mold 70 (in its second configuration) along the shaft of the endoscope 120 upward toward the patient's head and the esophagus 41 in the direction indicated by molding movement arrow 123, to a position where the mold 70 is proximate to the deteriorated gastroesophageal flap 55 (not shown) and a portion of the fundus 46 proximate to the cardiac notch 47. This movement is performed under visualization with the endoscope 120. A vacuum is applied to the vacuum lumen 79 and to the plurality of tissue gripping vacuum orifices 74. The vacuum orifices 74 grip, urge, and draw in a fold of musculo-mucosal tissue 115 into the mold 70, and hold the fold of tissue 115 against the molding surface 72. This molds the fold of tissue 115 into a shape related to a gastroesophageal flap (hereafter "molded stomach tissue") 125, such as the normal gastroesophageal flap 50 of GEFV 49. Typically, the fold of tissue 115 will include tissue of the wall of the fundus 46 near the cardiac notch 47 folded against the adjacent portion of the esophagus 41. While the fold of tissue 115 is illustrated as a fold of an entire thickness of tissue, the fold of tissue 115 may include less than the entire thickness of tissue, such as one or two layers. Prior to fixating the molded stomach tissue 125, the molded stomach tissue 125 may be viewed through a transparent portion of the mold 70 with the endoscope 120 to confirm that it meets the expectations of the endoscopist.

To fixate and secure the molded stomach tissue 125 in a shape approximating a gastroesophageal flap valve, at least one tissue fixation device 80 is deployed from the lumen orifice 84 in the manner described in conjunction with FIGS. 5-9. The tissue fixation devices 80 are typically preloaded into the lumens 82 of longitudinal member 62 prior to insertion of the mold 70 into the stomach 43. Typically, more than one tissue fixation device 80 is used. In an alternative embodiment, the tissue fixation devices 80 are deployed in a pattern to provide optimal fixation, such as an "M" or "C" or any other pattern, which may be repeated. In an alternative embodiment, the tissue fixation device is glue, or a substance provoking tissue regeneration or adhesion, which may be deployed individually, or in association with the mechanical tissue fixation devices 80. When used in association, the glue or provoking substance may be deposited between the tissues of the fold of tissue 115 to more firmly attach the tissues to each other, to increase the area of adhesions to improve the fixation, and to seal off the fixation sites.

Another step includes moving the mold 70 along the shaft of the endoscope 120 downward opposite to arrow 123, and toward the patient's feet and away from the esophagus 41 and the restored gastroesophageal flap valve, to a position where the fixated molded stomach tissue 125 may be inspected with the distal end 122 of the endoscope 120. If upon inspection the endoscopist is not satisfied that an acceptable restored gastroesophageal flap 127 has been formed, the mold 70 may be moved back into position for placement of additional tissue fixation devices 80, or for creating an additional molded tissue 125 and fixating.

A final step includes removal of the mold 70 from the patient. The mold 70 is moved from the second configuration to a third configuration for transoral removal, and removed from the patient by removing the longitudinal member 62. In an alternative embodiment, mold 70 comprises a material that may be passed "per vias naturales," i.e., by a natural process. The mold 70 is released from the longitudinal member 62 into the stomach for passage "per vias naturales," and the longitudinal member 62 is removed from the patient. In another alternative embodiment, the mold 70 can be left engaged temporarily with the fixated molded stomach tissue 125 to support the function of the restored GEFV 129, and protect it during healing. The mold 70 is arranged to disintegrate within a predetermined over time.

The steps described above are expected to result in a relatively uniformly shaped fold of tissue 115 because the mold 70 establishes the size of the fold of tissue 115 and molds the fold of tissue 115 into the molded stomach tissue 125 that approximates a normal gastroesophageal flap 50. The endoscopist does not need to decide how much tissue to take to form the fold of tissue 115 because the mold 70 standardizes and establishes these parameters.

The above procedure may also be performed with the longitudinal member 62 and the mold 70 being used in conjunction the endoscope 120, but not being moved over or physically guided by the shaft of the endoscope 120. In alternative embodiments, other visualization methods may be used, such as fluoroscopy with appropriate viewing marks on the devices.

FIG. 11 is a perspective cross-sectional view of a restored gastroesophageal flap 127 and a restored GEFV 129 according to an embodiment of the invention. FIG. 11 illustrates the restored gastroesophageal flap 127 formed by an embodiment of the invention described in conjunction with FIG. 10, after the mold 70 and the longitudinal member 62 have been removed from the vicinity of the gastroesophageal junction. At least one tissue fixation device 80, and preferably a plurality of tissue fixation devices 80, maintains the molded stomach tissue 125 as the restored gastroesophageal flap 127. The restored gastroesophageal flap 127 approximates the movement and functionality of the normal gastroesophageal flap 50. It opens and closes against the lesser curvature 45 portion of the stomach 43 in the manner of the normal gastroesophageal flap 50 described in conjunction with FIG. 1, thus forming a restored GEFV 129. The restored GEFV 129 is expected to approximate the functionality of the normal GEFV 49 described in conjunction with FIG. 1. The molding process described in conjunction with FIG. 10 is expected to produce a highly standardized procedure and outcome. Another advantage of the molding process is that the functionality of the normal GEFV 49 is reestablished upon conclusion of the procedure. There is no need to wait for adhesion to form a flap, or for a mounting device to biodegrade.

In addition to creating a restored gastroesophageal flap 127 and a restored GEFV 129, the embodiment of the invention described in conjunction with FIG. 10 also restores at least some of the other deteriorations associated with GERD that are illustrated in FIG. 2. The creation of the restored GEFV 125 also at least partially restores the cardiac notch 47 and makes the Angle of His 57 more acute. This moves the superior portion of the fundus 46 toward the mouth and away from where the esophagus 41 enters the stomach 43, restoring the arch of the normal fundus 46. This is expected to restore a patient's ability to burp air and gas. This is further expected to reduce the degree to which stomach contents reflux into the esophagus because the stomach contents are no longer presented with a funnel-like structure into the esophagus 41, as is the case with a Grade III or IV reflux appearance gastroesophageal flap 55.

Figure 12:
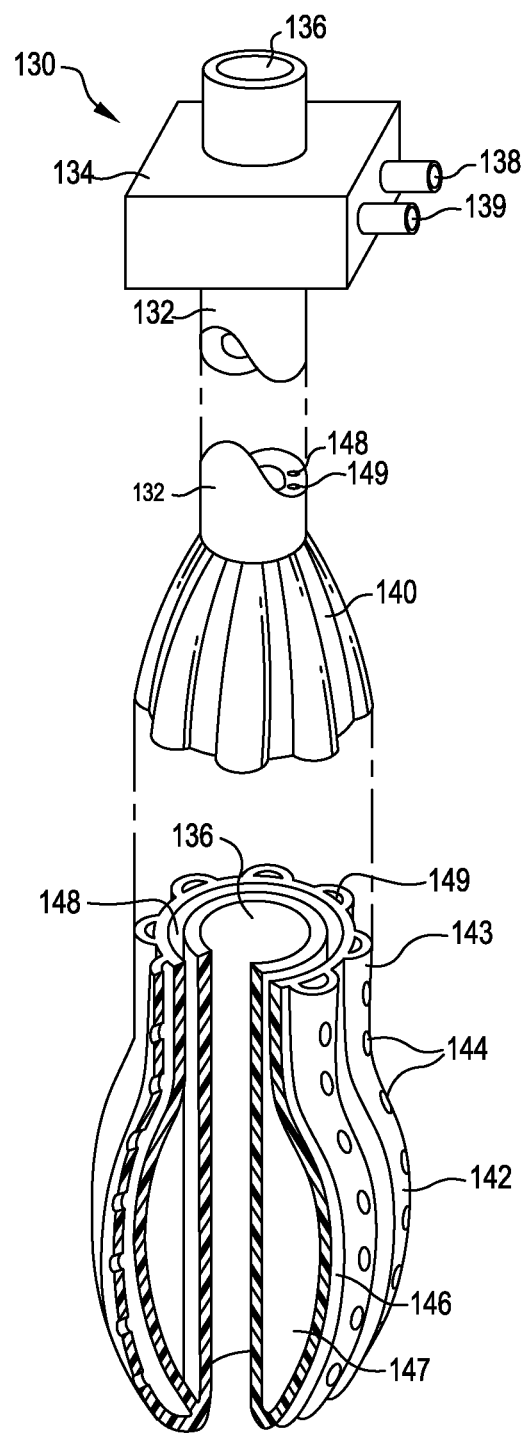
FIG. 12 is a perspective partial cross-section view of an invaginator device according to an embodiment of the invention.

FIG. 12 is a perspective partial cross-section view of an invaginator device 130 according to an embodiment of the invention. The invaginator device 130 includes an invaginator longitudinal member 132, an invaginator extracorporeal movement control member 134, an endoscope channel 136, a pressurized air port 138, a vacuum port 139, an invaginator-longitudinal member coupler 140, an invaginator surface 142, a longitudinal raised portions 143, a plurality of tissue gripping vacuum orifices 144, an invaginator member 146, an inflation member 147, an air pressure lumen 148, and a plurality of vacuum lumens 149.

The invaginator assembly 130 is a flexible structure arranged for gripping the walls of body lumens and hollow body structures, such as the esophagus and intestines. It is also arranged for endoscopic placement. The endoscope channel 136 of longitudinal member 132 is arranged to at least partially surround a length of the shaft of an endoscopic device, maintain an orientation relative to the shaft, and be movable along the shaft. While the invaginator device 130 has broad application for use with any body lumen or hollow structure, its features will be described with respect to a preferred embodiment for invaginating esophageal tissue in conjunction with restoration of a GEFV. Invaginator assembly 130 is arranged for transoral, endoscopic placement into the esophagus, and includes the endoscope channel 136 and the extracorporeal movement control member 134. In addition to being arranged to surround a length of the shaft of an endoscopic device, the endoscope channel 136 is also arranged to at least partially surround a length of the longitudinal member 62 of flap valve restoration assembly 60 illustrated in FIG. 3, maintain an orientation to the longitudinal member 62, and be movable along the longitudinal member 62. Longitudinal member 132 has sufficient flexibility for transoral placement into the stomach, and sufficient rigidity to manipulate structures carried by it and moved in opposition to it. Longitudinal member 62 may be made from any biocompatible material known in the art.

The extracorporeal invaginator movement control member 134 is attached to longitudinal member 132 and arranged to control the movements of the longitudinal member 132 and devices carried by it, including the invaginator member 146. Control member 134 includes a pressurized air port 138 and a vacuum port 139. While the control member 134 is illustrated as carrying the pressurized air port 138 and the vacuum port 139, these ports may be carried on the invaginator longitudinal member 132 or any other portion of the invaginator assembly 130. The control member 134 may be made from any biocompatible material known in the art.

The invaginator member 146 and its components are coupled to the invaginator longitudinal member 132 by the invaginator-longitudinal member coupler 140. The invaginator member 146 may have any shape. In a preferred embodiment, the invaginator member 146 is a generally cylindrical shape for ease of transoral insertion, and includes an inflation member 147, an air pressure lumen 148, and a vacuum lumen 149. The invaginator member 146 also includes an invaginator surface 142 having a plurality of longitudinal raised portions 143. At least one longitudinal raised portion 143 has a tissue gripper in the form of the plurality of tissue gripping vacuum orifices 144 served by a vacuum lumen 149 underlying the longitudinal raised portion 143. Only one longitudinal raised portion 143 is provided reference numbers in FIG. 12 for clarity. The plurality of tissue gripping vacuum orifices 144 are arranged to grip tissue by drawing, and tightly and releasably engaging the esophageal wall with the invaginator member 146. Once engaged, the invaginator assembly 130 can be used to impart a force to the vacuum gripped esophagus tissue to urge the engaged portion of the esophagus 41 in a direction selected by the endoscopist. The tissue gripping vacuum orifices 144 are coupled to a vacuum source by the vacuum port 139 and by a vacuum lumen 149. The vacuum level at the tissue gripping vacuum orifices 144 is controlled by a regulator (not shown). In an alternative embodiment, the invaginator member 146 may be only a portion of a generally cylindrically shaped structure. For example, the invaginator member 146 may be carried on the longitudinal member 63 of FIG. 3, and arranged to only engage approximately one-half of the interior perimeter of the esophagus. In an alternative embodiment, the invaginator tissue gripper may comprise a peripheral surface arranged to non-invasively and frictionally engage tissue, such as a fish scale-like structure similar to that used on the bases of cross country skis, or a plurality of protrusions.

Invaginator member 146 has a first configuration for transoral placement through the mouth, down into the esophagus, and into proximity to the LES 48. The first configuration is a collapsed shape dimensioned for transoral placement. In a preferred embodiment, the collapsed shape maintains the endoscopic channel 136 so that the collapsed invaginator member 146 may be transorally guided by an endoscope shaft. Invaginator member 146 has a second configuration, which has a shape related to the cross-sectional dimensions of the esophagus 41. Invaginator member 146 is moved from the first configuration to the second configuration in vivo. Methods for moving from the first configuration to the second configuration include applying a pressure to expand the inflation member 147, and a mechanical means. The pressure can be supplied by compressed air or pressurized fluid. An embodiment of the invention is illustrated that includes application of air pressure to expand the inflation member 146 by inflation, and move the invaginator member 146 from a first configuration to a second configuration. The invaginator device 130 includes a pressurized air port 138, a regulator (not shown) to provide a controlled air pressure, and an inflation member 147. The inflation member 147 is coupled to the controlled air pressure by an air pressure lumen 148, and application of air pressure causes the invaginator member 146 to move from the first configuration to the second configuration. The invaginator member 146 is arranged to move from the second configuration to a third configuration for removal from the patient. The movement to the third configuration may be by releasing the air pressure from the inflation member 147. The third configuration may be similar to the first configuration. The invaginator member 146 is made from any biocompatible material known in the art. In an alternative embodiment, the invaginator device 130 may be coupled to an endoscopic device, and the endoscopic device used to maneuver the invaginator device 130.

Figure 13:
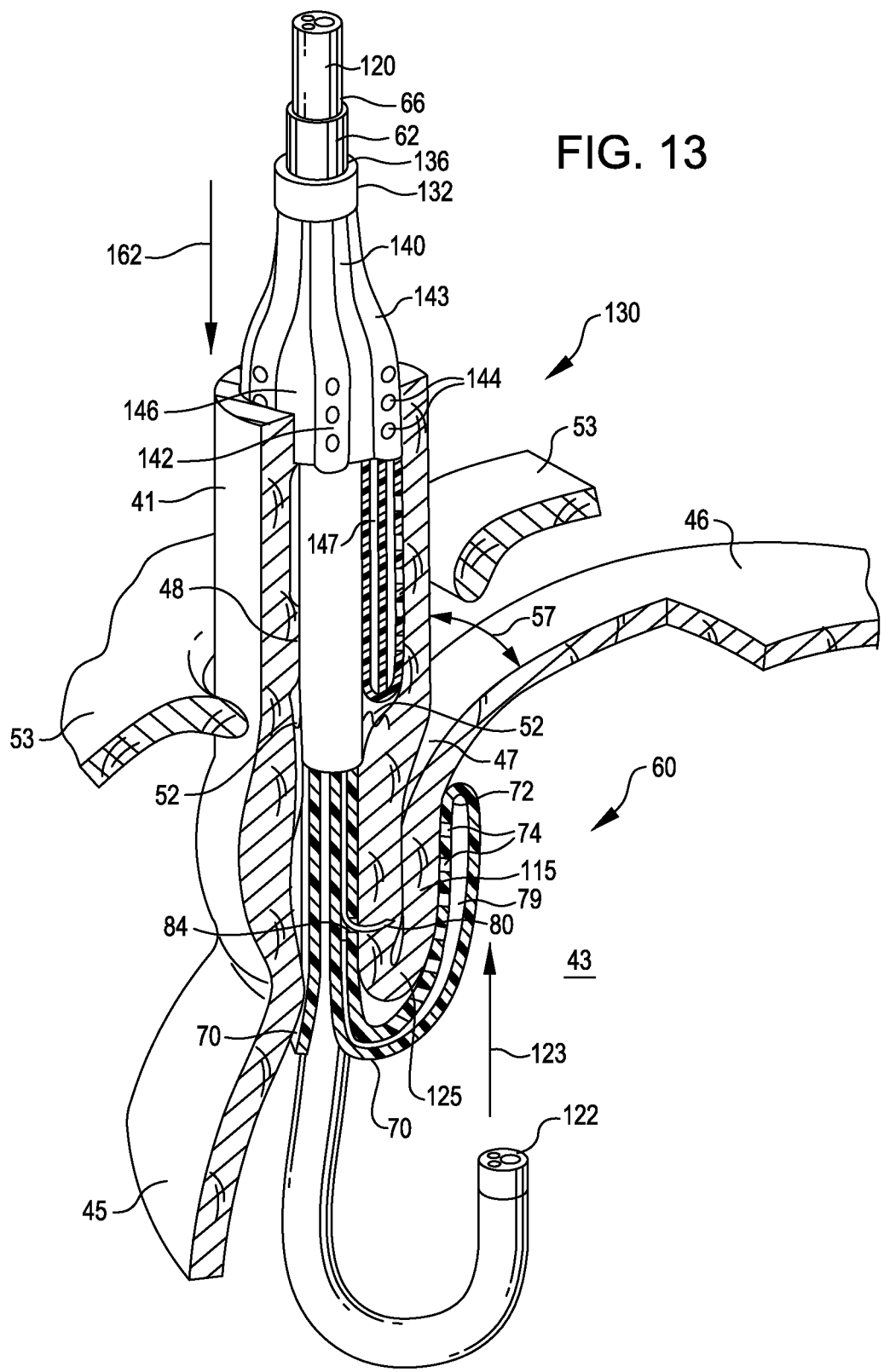
FIG. 13 is a perspective cross-sectional view of the gastroesophageal flap valve restoration assembly of FIG. 3 and the invaginator assembly of FIG. 12 being used to transorally restore a gastroesophageal flap valve employing an endoscopic visualization device, according to an embodiment of the invention.

FIG. 13 is a perspective cross-sectional view of the GEFV restoration assembly 60 of FIG. 3 and the invaginator assembly 130 of FIG. 12 being used to transorally restore a gastroesophageal flap valve employing an endoscopic visualization device 120, according to an embodiment of the invention. FIG. 13 illustrates the invaginator device 130 providing movement of and control over the esophagus 41 in combination with the GEFV restoration assembly 60 for transoral restoration of a gastroesophageal flap valve. The portions toward the patient's mouth of the shaft of the endoscope 120, the invaginator longitudinal member 132, and the longitudinal member 62 are truncated in FIG. 13 for clarity. The procedure is similar to that described in conjunction with FIG. 10. Preferably, prior to moving the mold 70 toward to the patient's head in the direction of arrow 123, the invaginator device 130 with the invaginator member 146 in its first configuration for placement is lowered into the esophagus 41. The invaginator longitudinal member 132 is engaged with and slid along the shaft of the endoscope 120 and the longitudinal member 62 of the GEFV restoration assembly 60 as a guide to a position preferably toward the patient's mouth from the LES 48.

Invaginator member 146 is then moved in vivo from the first configuration to the second configuration by application of air pressure to the inflation member 147 for vacuum engagement of the esophagus. Another step includes application of a vacuum to the vacuum lumen 149 and correspondingly to the plurality of tissue gripping vacuum orifices 144 in the longitudinal raised portions 143. In response to the applied vacuum, the plurality tissue gripping vacuum orifices 144 draw in, and tightly and releasably engage the esophageal wall with the invaginator member 146. A force in the invagination movement direction 162 is applied to invaginator extracorporeal movement control member 134 to push the lower portion of esophagus 41 and the gastroesophageal junction 52 (not shown) toward and partially invaginated into the stomach 43. This moves stomach tissue generally, and particularly a portion of the fundus 46, into an improved position for restoration of the GEFV. The invagination aids in creating the fold of tissue 115 by partially pre-forming the fundus tissue, and by improving the position and presentment of the fundus tissue to the mold 70. The endoscopist is likely to need the invaginator device 130 to create the fold of tissue 115 when a Grade IV GEFV is being restored. The invaginator device 130 may not be needed when a Grade II or Grade III GEFV is being restored. Once a restored GEFV 129 has been formed, the invaginator member 146 is moved from the second position to the third position for removal, and the invaginator device 130 is removed from the patient.

The next three figures illustrate another gastroesophageal flap valve restoration device according to another embodiment of the invention. FIGS. 14 and 16 are perspective partial-sectional views of a gastroesophageal flap valve restoration assembly 200 with a moveable tissue gripper, according to an embodiment of the invention. FIG. 14 illustrates GEFV restoration assembly 200 with the moveable tissue gripper 210 in its extended configuration. FIG. 15 is a cross-sectional plan view of the mold 230 of FIG. 14. FIG. 16 illustrates GEFV restoration assembly 200 with the moveable tissue gripper 210 in its retracted/molding configuration. GEFV restoration assembly 200 includes a longitudinal member 202, an endoscopic channel 66, a non-invasive tissue gripper 210, a tissue gripper control member 211, a vacuum port 139, a movable arm 212, a plurality of tissue gripping orifices 214, a vacuum gripping surface 216, a bending portion 218, a mold 230, a bending guide surface 232, and a molding surface 234. FIGS. 14 and 16 do not illustrate the extracorporeal portions of the endoscope 120 and the longitudinal member 202, which are truncated for clarity.

Longitudinal member 202 is substantially similar to longitudinal member 62 of GEFV restoration assembly 60 described in conjunction with FIG. 3. The longitudinal member 202 carries the mold 230 and the moveable arm 212 on its distal end for placement within the stomach. For purposes of clarity, FIGS. 14 and 16 do not illustrate the plurality of lumens 82a-e arranged to carry tissue fixation devices 80 for deployment from the plurality of lumen orifices 84a-e, and do not illustrate the extracorporeal movement control member 64.

The tissue gripper 210 includes the tissue gripper control member 211, the vacuum port 139, the moveable arm 212, the plurality of tissue gripping vacuum orifices 214, the vacuum gripping surface 216, and the bending portion 218. The tissue gripper control member 211 is carried in a lumen (not shown) in longitudinal member 202. The bending portion 218 joins the tissue gripper control member 211 and the moveable arm 212, and is arranged to bend over a range of about 90 degrees. The arm 212 carries vacuum gripping surface 216, which in turn carries the plurality of tissue gripping vacuum orifices 214. The tissue gripping vacuum orifices 214 are vacuum coupled to the vacuum port 139 by a vacuum lumen (not shown) running through the moveable arm 212, the bending portion 218, and the control member 211. In an alternative embodiment, the vacuum coupling may include a vacuum lumen that bypasses the bending portion 218. The plurality of tissue gripping vacuum orifices 214 are arranged to grip tissue by drawing in, and tightly and releasably engaging proximate tissue with the vacuum gripping surface 216. Once engaged, the tissue gripper 210 can be used to impart a force to the vacuum gripped tissue to urge the gripped tissue and surrounding tissue in a manner selected by the endoscopist.

The moveable arm 212 of the tissue gripper 210 is arranged to be movable by moving control member 211 longitudinally relative to the longitudinal member 202. FIG. 14 illustrates the tissue gripper 210 with the moveable arm 212 in an extended configuration for gripping tissue. FIG. 16 illustrates the moveable arm 212 of the tissue gripper 210 in the retracted/molding configuration. The moveable arm 212 is moved from the extended configuration of FIG. 14 to the retracted/molding configuration illustrated in FIG. 16 by moving tissue gripper control member 211 distally and longitudinally toward the mold 230. The movement of control member 211 distally forces the moveable arm 212 against bending guide surface 232, which in turn exerts a bending force against bending portion 218. Continued movement of control member 211 increases the bend in the bending portion 218 and moves the moveable arm 212 to the retracted/molding configuration. The bending guide surface 232 is arranged to control the position of the moveable arm 212 relative to the longitudinal member 202, so that the moveable arm 212 in the retracted/molding configuration holds the fold of tissue 115 proximate to the longitudinal member 202 and drawn into and against the molding surface 234. The extension of moveable arm 212 is by moving the control member 211 proximally. The tissue gripper 210 is arranged to non-invasively grip and move a fold of tissue 115 into the mold 230. The tissue gripper 210 brings the tissues in the fold of tissue 115 close together for fixation. In an alternative embodiment, the molding configuration of the moveable arm 212 includes moving the vacuum gripping surface 216 an additional distance distally to a position where the vacuum gripping surface 216 is distal of the bending guide surface 232. In an alternative embodiment, the tissue gripper 210 can be arranged to draw a fold of tissue 115 into the mold 70 of FIG. 3 by making provision for and carrying the tissue gripper 210 with longitudinal member 62.

FIG. 15 illustrates the mold 230 carried on the distal end of the longitudinal member 202. Endoscope 120 and tissue gripper 210 are omitted from FIG. 15 for clarity. The mold 230 is a semicircular structure that includes the bending guide surface 232 and the molding surface 234, and is arranged for causing stomach tissue to assume a shape related to a gastroesophageal flap. The molding surface 234 has an approximately 180 degree, semicircular shape related to the normal gastroesophageal flap 50. In alternative embodiments, the molding surface 234 may be configured to form a semicircular structure having with a semicircular arc varying between approximately 90 degrees and 360 degrees. The molding surface 234 is arranged to have a fold of tissue 115 drawn into it by the tissue gripper 210, thereby molding that fold of tissue 115 into molded stomach tissue 125. The molding surface 234 is formed to replicate the normal gastroesophageal flap 50. In an alternative embodiment, the mold 230 has a first collapsed configuration for transoral placement into the stomach 43, and a second configuration having a shape related to the gastroesophageal flap.

Figure 17:
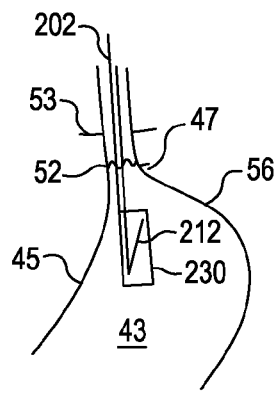
FIGS. 17-22 are sequential, schematic cross-sectional views illustrating the gastroesophageal flap valve restoration assembly of FIGS. 14-16 being used to transorally restore a gastroesophageal flap valve, according to an embodiment of the invention.

FIGS. 17-22 are schematic cross-sectional views illustrating the GEFV restoration assembly with tissue gripper 200 of FIGS. 14-16 being used to transorally restore a gastroesophageal flap valve, according to an embodiment of the invention. The restoration is similar to that described in conjunction with FIG. 10, and uses the endoscope 120 for visualization and as a guide for placing the distal end of the longitudinal member 202 in the stomach 43. FIG. 17 illustrates an initial step where the distal portion of the longitudinal member 202 carrying the tissue gripper 210 and the mold 230 is placed in the stomach 43. The moveable arm 212 is in a first configuration for insertion, which is the retracted/molding configuration.

Figure 18:
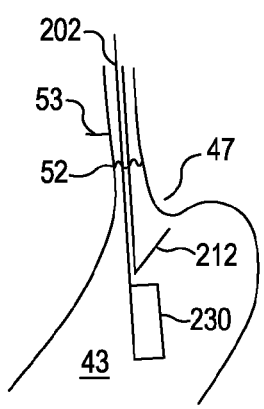

FIG. 18 illustrates an intermediate step where the moveable arm 212 is moved from the first retracted/molding configuration position to the second gripping configuration for gripping and moving a fold of tissue 115. The movement of the moveable arm 212 is by manipulation of the tissue gripper control member 211. Under visualization of the endo scope 120, the moveable arm 212 is placed in proximity to target tissue of the fundus 46 that is proximate to the cardiac notch 47 and selected by the endoscopist as suitable for restoration of the GEFV 49. A vacuum is applied to the tissue gripping vacuum orifices 214, causing the vacuum gripping surface 216 to grip the target tissue by vacuum drawing in, and tightly and releasably engaging the target tissue. The vacuum gripped target tissue and tissue proximate to it form the fold of tissue 115.

Figure 19:
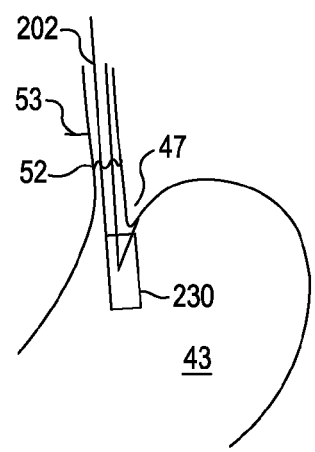
Figure 20:
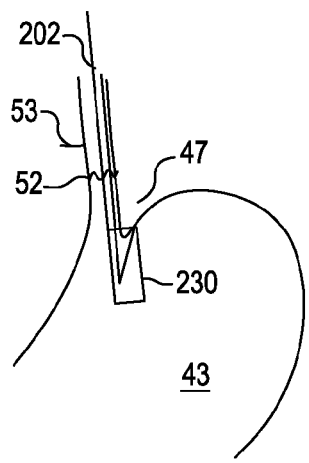

FIG. 19 illustrates an intermediate step where the moveable arm 212, while vacuum gripping the target tissue, is partially moved from the second gripping configuration to the first retracted/molding configuration and toward the mold 230. FIG. 20 illustrates another intermediate step where the moveable arm 212, while vacuum gripping the target tissue, is moved further to the first retracted/molding configuration and partially into the mold 230.

Figure 21:
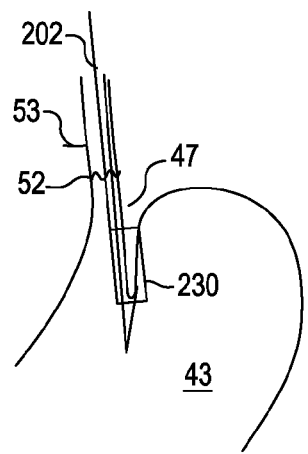
Figure 22:
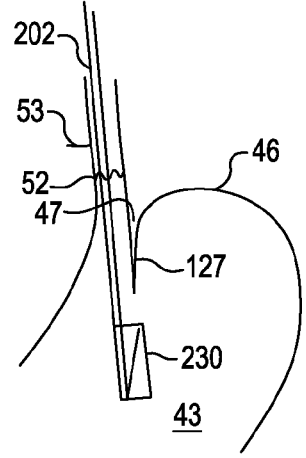

FIG. 21 illustrates still another intermediate step where the moveable arm 212, while vacuum gripping the target tissue, has been moved to the first retracted/molding configuration and fully into the mold 230. Upon being moved fully into the mold 230 as illustrated by FIG. 21, the molding surface 234 of mold 230 brings the tissues comprising the fold of tissue 115 close together, and causes the fold of tissue 115 to assume a shape related to a gastroesophageal flap (molded stomach tissue 125). The fold of tissue 115 does not include the gastroesophageal junction 52 or any tissue oral of the gastroesophageal junction 52. To fixate and secure the molded stomach tissue 125, at least one tissue fixation device 80 is deployed from the lumen orifice 84 (not shown) in the manner described in conjunction with FIGS. 5-9, and 10. The fixation maintains the shaped stomach tissue in a shape approximating a gastroesophageal flap (restored gastroesophageal flap 127) as illustrated in FIG. 11. FIG. 22 illustrates a final step where the mold 230 and moveable arm 212 are moved distally into the stomach 43 for inspection by the endoscopist. A final step includes removal of the mold 230 and the moveable arm 212 from the patient.

Figure 23:
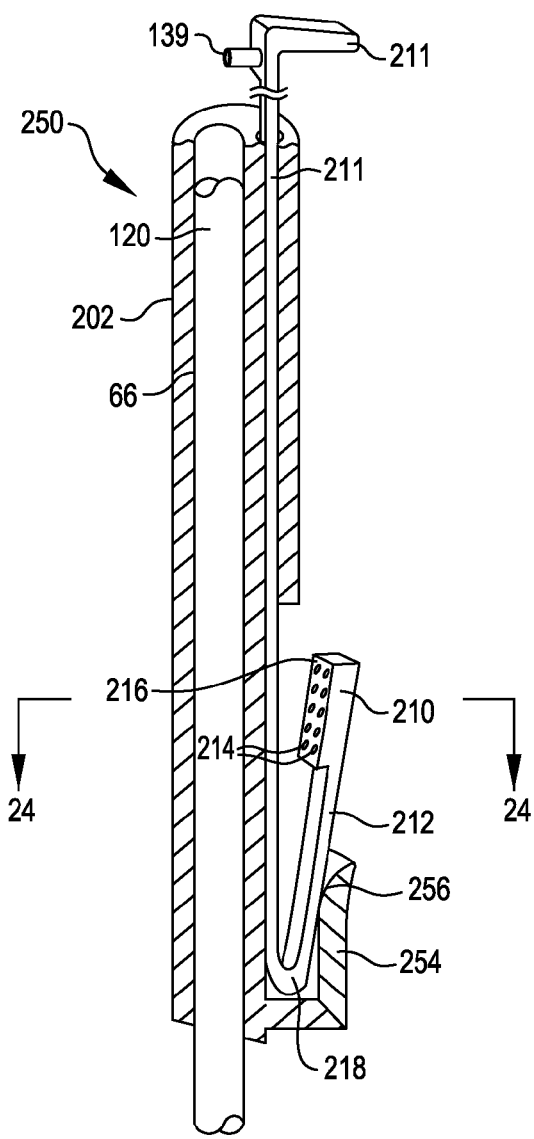
FIG. 23 is a perspective partial-sectional view of a gastroesophageal flap valve restoration assembly with a tissue gripper guide in its retracted/molding configuration, according to an embodiment of the invention.

FIG. 23 is a perspective partial-sectional view of a gastroesophageal flap valve restoration assembly 250 with a tissue gripper guide in its retracted/molding configuration, according to an embodiment of the invention. The gastroesophageal flap valve restoration assembly 250 is similar in construction and operation to the flap valve restoration assembly 200. The restoration assembly 250 includes a guide support 254 and a guide surface 256, but does not include the mold 230 of FIG. 14. The restoration assembly 250 uses the tissue gripper 210 as a tissue shaper to cause stomach tissue to assume a shape related to a gastroesophageal flap 50. Guide support 254 is carried on longitudinal member 202, and the guide surface 256 is arranged to control the position of the moveable arm 212 relative to the longitudinal member 202, so that the moveable arm 212 in the retracted/molding configuration holds the fold of tissue 115 proximate to the longitudinal member 202.

FIG. 24 is a cross-sectional view illustrating the gastroesophageal flap valve restoration assembly 250 of FIG. 23 being used to transorally restore a gastroesophageal flap valve, according to an embodiment of the invention. Restoration of the gastroesophageal flap with the gastroesophageal flap valve restoration assembly 250 is similar to the restoration of the gastroesophageal flap with the flap valve restoration assembly 200 described in conjunction with FIGS. 17-22. The restoration begins to differ at FIG. 21, the point where the moveable arm 212 is in the retracted/molding configuration and is holding the fold of tissue 115 proximate to the longitudinal member 202 in an initial shaping position 258. As illustrated in FIG. 24, the longitudinal member 202 and the movable arm 212 become the tissue shaper of this embodiment, and cause the gripped stomach tissue to assume a shape related to a gastroesophageal flap. A plurality of tissue gripping steps is used to cause the fold of tissue 115 to assume a shape related to a gastroesophageal flap. At least one tissue fixation device 80 is deployed into the fold of tissue 115 at the initial shaping position 258. The vacuum applied to the plurality of tissue gripping vacuum orifices 214 is reduced to disengage the vacuum gripping surface 216 from the fold of tissue 115, and the moveable arm 212 may be moved away from the fold of tissue 115. The longitudinal member 202, which carries the tissue gripper 210 and the guide support 254, is rotated to another shaping position 259. The vacuum is reapplied to the plurality tissue gripping vacuum orifices 214 to engage the vacuum gripping surface 216 with the fold of tissue 115, and the movable arm 212 is moved to retracted/molding configuration. At least one tissue fixation device 80 is deployed into the fold of tissue 115 at the another shaping position 259. The movement, shaping, and fixation of tissue in a shape approximating a gastroesophageal flap continues until a restored gastroesophageal flap 127 is formed. The restoration is viewed from a retroflexed endoscope, and the endoscopist is able to inspect each step. Once the endoscopist is satisfied that a restored GEFV 49 has been formed, as illustrated in FIG. 11, a final step includes removal of the gastroesophageal flap valve restoration assembly 250 from the patient.

Figure 25:
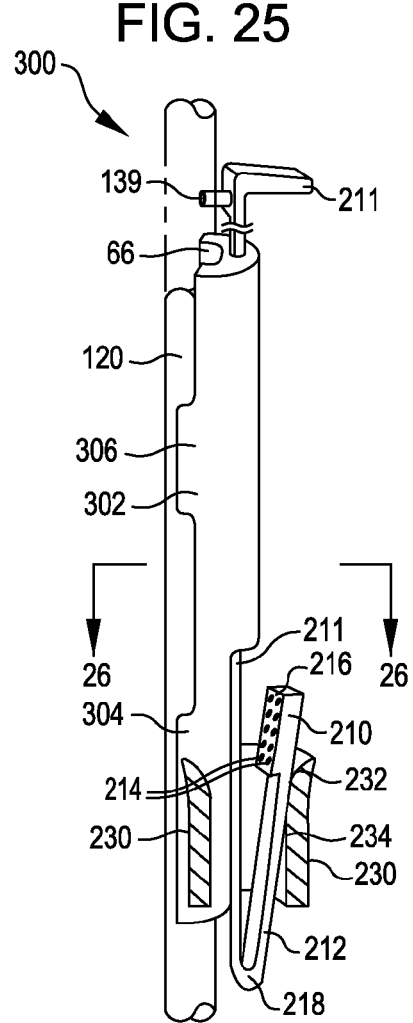
FIG. 25 is perspective partial-sectional view of a gastroesophageal flap valve restoration assembly of FIGS. 14-16 arranged to engage an extracorporeal portion of an endoscopic device when a portion of the endoscopic device is in vivo, according to an embodiment of the invention.

FIG. 25 is perspective partial-sectional view of a gastroesophageal flap valve restoration assembly of FIGS. 14-16 arranged to engage an extracorporeal portion of an endoscopic device when a portion of the endoscopic device is in vivo, according to an embodiment of the invention. FIG. 26 is a perspective partial cross-sectional view of gastroesophageal flap valve restoration assembly 300. Gastroesophageal flap valve restoration assembly 300 includes a longitudinal member 302, which includes a retention portion 304, and in an alternative embodiment at least one other retention portion 306.

The endoscopic channel 66 of longitudinal member 302 is round but does not close along its length, allowing the restoration assembly 300 to be removably engaged with a portion of the shaft of an endoscopic device 120 when the retroflexed end 122 is in vivo. The endoscopic channel 66 of longitudinal member 302 is dimensioned to partially surround a length or a portion of a shaft of an endoscopic device 120. The retention portions 304 and 306 are arranged to allow longitudinal member 302 to engage the shaft of an endoscopic device 120, to retain the engagement until disengaged by the endoscopist, and to allow the longitudinal member 302 to be moveable relative to the shaft of the engaged endoscope 120. In an alternative embodiment, the gastroesophageal flap valve restoration assembly 300 includes a plurality of longitudinal shims to match the diameter of the endoscopic channel 66 to the diameter of the endoscope shaft.

The ability to engage the longitudinal member 302 of gastroesophageal flap valve restoration assembly 300 with the shaft of an endoscope 120 allows an endoscopist to first endoscopically view the stomach 43 and GEFV 49 to determine whether restoration is indicated. When restoration is indicated, the endoscopist can then engage the longitudinal member 302 with the shaft of the endoscope 120 without removing the retroflexed tip (distal end) of the endoscope 122 from the stomach 43. The gastroesophageal flap valve restoration assembly 300 is then moved down the shaft of the endoscope 120 and into position for restoration of the gastroesophageal flap.

The arrangement providing an ability to engage a longitudinal member of a gastroesophageal flap valve restoration assembly with an endoscope without removing the retroflexed tip of the endoscope from the stomach may be used for any of the devices described herein. Extracorporeal movement control members, such as member 64 of FIG. 3, may require an opening to allow the shaft of the endoscope 120 to fully enter the endoscopic channel 66.

Although the present invention has been described in considerable detail with reference to certain preferred embodiments, other embodiments are possible. Therefore, the spirit or scope of the appended claims should not be limited to the description of the embodiments contained herein. It is intended that the invention resides in the claims hereinafter appended.

What is claimed is:

1. A method of forming a fold in stomach tissue using a transoral assembly, the method comprising:
   positioning a transoral assembly in a stomach transorally, the assembly having a mold configured to receive stomach tissue, the mold having an internal volume, a tissue shaper that non-invasively grips and urges stomach tissue into the mold, at least one tissue fixation device, and
   a longitudinal member a portion of which is arranged to carry the mold and the tissue, shaper, the mold being positioned distal to an intersection of the stomach and the esophageal tract;
   expanding the mold after the positioning step;
   drawing stomach tissue into the internal volume of the mold after the expanding step; and
   deploying the at least one tissue fixation device through the stomach tissue held, by the mold thereby forming a fold using the stomach tissue.

2. The method of claim 1, wherein
   the positioning step is carried out with the mold having a first configuration for transoral placement in proximity to the esophageal-gastric junction, and a second configuration for receiving stomach tissue;
   the expanding step being carried out with the mold moving from the first configuration to the second configuration.

3. The method of claim 2, wherein:
   the positioning step is carried out with the mold being arranged to move from a first configuration to a second configuration in response to a change in pressure in a portion of the mold; and
   the expanding step is carried out by changing the pressure in the portion of the mold.

4. The method of claim 1, wherein:
   the positioning step is carried out with the assembly including an invaginator having a member configured to vacuum grip an interior surface of an esophagus from within the esophagus and allow an invaginating force to be imparted substantially parallel to a longitudinal axis of the esophagus.

5. The assembly of claim 1, wherein:
   the drawing step is carried out with the tissue shaper gripping the stomach tissue with a vacuum.

6. The method of claim 1, wherein:
the positioning step is carried out with the tissue shaper being movable with respect to the mold.

7. The method of claim 1, wherein:
the positioning step is carried out with the mold including a fixed portion and a moveable portion.

8. The method of claim 7, further comprising the step of:
bringing the moveable portion together with the fixed portion thereby molding the stomach tissue.

9. The method of claim 1, wherein:
the drawing step is carried out by drawing stomach tissue into the mold along a plane parallel to a molding surface.

10. The method of claim 1, wherein:
the drawing step is carried out with the stomach tissue drawn into the mold being fundus tissue distal to the intersection of the stomach and the esophageal tract.

11. The method of claim 10, wherein:
the drawing step is carried out with the fundus tissue forming both sides of the fold.

* * * * *